(12) United States Patent
Goodman et al.

(10) Patent No.: US 9,649,151 B2
(45) Date of Patent: May 16, 2017

(54) END EFFECTOR ASSEMBLIES AND METHODS OF MANUFACTURING END EFFECTOR ASSEMBLIES FOR TREATING AND/OR CUTTING TISSUE

(71) Applicant: COVIDIEN LP, Mansfield, MA (US)

(72) Inventors: Kelley D. Goodman, Erie, CO (US); Keir Hart, Lafayette, CO (US); Susan Hiebert, Lyons, CO (US); Geneva Ladtkow, Arvada, CO (US); Weng-Kai K. Lee, Longmont, CO (US); Prakash Manley, Lafayette, CO (US); Arlen J. Reschke, Longmont, CO (US); Amanda K. White, Port Orchard, WA (US)

(73) Assignee: COVIDIEN LP, Mansfield, MA (US)

( * ) Notice: Subject to any disclaimer, the term of this patent is extended or adjusted under 35 U.S.C. 154(b) by 537 days.

(21) Appl. No.: 14/202,145

(22) Filed: Mar. 10, 2014

(65) Prior Publication Data

US 2014/0353869 A1 Dec. 4, 2014

Related U.S. Application Data

(60) Provisional application No. 61/829,415, filed on May 31, 2013.

(51) Int. Cl.
*A61B 18/14* (2006.01)
*A61B 17/00* (2006.01)
*A61B 18/00* (2006.01)

(52) U.S. Cl.
CPC ...... *A61B 18/1445* (2013.01); *A61B 18/1442* (2013.01); *A61B 2017/00526* (2013.01);
(Continued)

(58) Field of Classification Search
CPC ............ A61B 18/1442; A61B 18/1445; A61B 2017/00526
See application file for complete search history.

(56) References Cited

U.S. PATENT DOCUMENTS

D249,549 S 9/1978 Pike
D263,020 S 2/1982 Rau, III
(Continued)

FOREIGN PATENT DOCUMENTS

CN 201299462 9/2009
DE 2415263 A1 10/1975
(Continued)

OTHER PUBLICATIONS

European Search Report from corresponding EP 14169456 dated Oct. 22, 2014.
(Continued)

*Primary Examiner* — James Sanders

(57) ABSTRACT

A method of manufacturing an end effector assembly including first and second energizable portions configured to supply energy to tissue is provided. The method includes forming a substrate including first and second portions interconnected by a connector portion. The substrate is formed as a single integrated component. The method further includes engaging the substrate with an insulative member, and removing the connector portion of the substrate to electrically insulate the first and second portions from one another.

20 Claims, 5 Drawing Sheets

(52) U.S. Cl.
CPC ........... *A61B 2018/0063* (2013.01); *A61B 2018/00607* (2013.01)

(56) References Cited

U.S. PATENT DOCUMENTS

| | | |
|---|---|---|
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| 5,344,005 A * | 9/1994 | Kettner ............ A61B 17/06138 206/63.3 |
| D354,564 S | 1/1995 | Medema |
| D358,887 S | 5/1995 | Feinberg |
| D384,413 S | 9/1997 | Zlock et al. |
| H1745 H | 8/1998 | Paraschac |
| D402,028 S | 12/1998 | Grimm et al. |
| D408,018 S | 4/1999 | McNaughton |
| D416,089 S | 11/1999 | Barton et al. |
| D424,694 S | 5/2000 | Tetzlaff et al. |
| D425,201 S | 5/2000 | Tetzlaff et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| 7,150,097 B2 | 12/2006 | Sremcich et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinge |
| D541,938 S | 5/2007 | Kerr et al |
| D545,432 S | 6/2007 | Watanabe |
| D547,154 S | 7/2007 | Lee |
| 7,270,664 B2 | 9/2007 | Johnson et al. |
| 7,276,068 B2 | 10/2007 | Johnson et al. |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| D649,249 S | 11/2011 | Guerra |
| D649,643 S | 11/2011 | Allen, IV et al. |
| D661,394 S | 6/2012 | Romero et al. |
| 8,333,765 B2 | 12/2012 | Johnson et al. |
| RE44,834 E | 4/2014 | Dumbauld et al. |
| 2006/0271038 A1 | 11/2006 | Johnson et al. |
| 2011/0046623 A1 | 2/2011 | Reschke |
| 2011/0073246 A1 | 3/2011 | Brandt et al. |
| 2011/0178519 A1 | 7/2011 | Couture et al. |
| 2012/0259331 A1 | 10/2012 | Garrison |
| 2013/0046303 A1 | 2/2013 | Evans et al. |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 3627221 A1 | 2/1988 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1281878 A1 | 2/2003 |
| EP | 1159926 A3 | 3/2003 |
| EP | 1958583 A2 | 8/2008 |
| EP | 2301467 | 3/2011 |
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 9-10223 C | 1/1997 |
| JP | 09000538 A | 1/1997 |
| JP | 9-122138 A | 5/1997 |
| JP | 0010000195 A | 1/1998 |
| JP | 10-155798 A | 6/1998 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000-135222 A | 5/2000 |
| JP | 2000342599 A | 12/2000 |
| JP | 2000350732 A | 12/2000 |
| JP | 2001008944 A | 1/2001 |
| JP | 2001029356 A | 2/2001 |
| JP | 2001-03400 | 4/2001 |
| JP | 2001128990 A | 5/2001 |
| JP | 2001-190564 A | 7/2001 |
| JP | 2002-136525 A | 5/2002 |
| JP | 2002-528166 A | 9/2002 |
| JP | 2003-116871 A | 4/2003 |
| JP | 2003-175052 A | 6/2003 |
| JP | 2003245285 A | 9/2003 |
| JP | 2004-517668 A | 6/2004 |
| JP | 2004-528869 A | 9/2004 |
| JP | 2005-152663 A | 6/2005 |
| JP | 2005-253789 A | 9/2005 |

(56) References Cited

FOREIGN PATENT DOCUMENTS

| | | | |
|---|---|---|---|
| JP | 2005312807 A | 11/2005 | |
| JP | 2006-015078 A | 1/2006 | |
| JP | 2006-501939 A | 1/2006 | |
| JP | 2006-095316 A | 4/2006 | |
| JP | 2011125195 A | 6/2011 | |
| SU | 401367 A1 | 10/1973 | |
| WO | 0036986 A1 | 6/2000 | |
| WO | 0059392 A1 | 10/2000 | |
| WO | 0115614 A1 | 3/2001 | |
| WO | 0154604 A1 | 8/2001 | |
| WO | 02045589 A3 | 9/2002 | |
| WO | 2006/021269 A1 | 3/2006 | |
| WO | 2005110264 A3 | 4/2006 | |
| WO | 2008/040483 A1 | 4/2008 | |
| WO | 2011/018154 A1 | 2/2011 | |

OTHER PUBLICATIONS

Michael Choti, "Abdominoperineal Resection with the LigaSure Vessel Sealing System and LigaSure Atlas 20 cm Open Instrument"; Innovations That Work, Jun. 2003.

Chung et al., "Clinical Experience of Sutureless Closed Hennorrhoidectomy with LigaSure" Diseases of the Colon & Rectum vol. 46, No. 1 Jan. 2003.

Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.

Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.

Peterson et al. "Comparison of Healing Process Following Ligation with Sutures and Bipolar Vessel Sealing" Surgical Technology International (2001).

"Electrosurgery: A Historical Overview" Innovations in Electrosurgery; Sales/Product Literature; Dec. 31, 2000.

Johnson et al. "Evaluation of a Bipolar Electrothermal Vessel Sealing Device in Hemorrhoidectomy" Sales/Product Literature; Jan. 2004.

E. David Crawford "Evaluation of a New Vessel Sealing Device in Urologic Cancer Surgery" Sales/Product Literature 2000.

Johnson et al. "Evaluation of the LigaSure Vessel Sealing System in Hemorrhoidectormy" American College of Surgeons (ACS) Clinicla Congress Poster (2000).

Muller et al., "Extended Left Hemicolectomy Using the LigaSure Vessel Sealing System" Innovations That Work, Sep. 1999.

Kennedy et al. "High-burst-strength, feedback-controlled bipolar vessel sealing" Surgical Endoscopy (1998) 12: 876-878.

Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.

Carus et al., "Initial Experience With the LigaSure Vessel Sealing System in Abdominal Surgery" Innovations That Work, Jun. 2002.

Heniford et al. "Initial Research and Clinical Results with an Electrothermal Bipolar Vessel Sealer" Oct. 1999.

Heniford et al. "Initial Results with an Electrothermal Bipolar Vessel Sealer" Surgical Endoscopy (2000) 15:799-801.

Herman et al., "Laparoscopic Intestinal Resection With the LigaSure Vessel Sealing System: A Case Report"; Innovations That Work, Feb. 2002.

Koyle et al., "Laparoscopic Palomo Varicocele Ligation in Children and Adolescents" Pediatric Endosurgery & Innovative Techniques, vol. 6, No. 1, 2002.

W. Scott Helton, "LigaSure Vessel Sealing System: Revolutionary Hemostasis Product for General Surgery"; Sales/Product Literature 1999.

LigaSure Vessel Sealing System, the Seal of Confidence in General, Gynecologic, Urologic, and Laparaoscopic Surgery; Sales/Product Literature; Apr. 2002.

Joseph Ortenberg "LigaSure System Used in Laparoscopic 1st and 2nd Stage Orchiopexy" Innovations That Work, Nov. 2002.

Sigel et al. "The Mechanism of Blood Vessel Closure by High Frequency Electrocoagulation" Surgery Gynecology & Obstetrics, Oct. 1965 pp. 823-831.

Sampayan et al, "Multilayer Ultra-High Gradient Insulator Technology" Discharges and Electrical Insulation in Vacuum, 1998. Netherlands Aug. 17-21, 1998; vol. 2, pp. 740-743.

Paul G. Horgan, "A Novel Technique for Parenchymal Division During Hepatectomy" The American Journal of Surgery, vol. 181, No. 3, Apr. 2001 pp. 236-237.

Benaron et al., "Optical Time-of-Flight and Absorbance Imaging of Biologic Media", Science, American Association for the Advancement of Science, Washington, DC, vol. 259, Mar. 5, 1993, pp. 1463-1466.

Olsson et al. "Radical Cystectomy in Females" Current Surgical Techniques in Urology, vol. 14, Issue 3, 2001.

Palazzo et al. "Randomized clinical trial of Ligasure versus open haemorrhoidectomy" British Journal of Surgery 2002, 89, 154-157.

Levy et al. "Randomized Trial of Suture Versus Electrosurgical Bipolar Vessel Sealing in Vaginal hysterectomy" Obstetrics & Gynecology, vol. 102, No. 1, Jul. 2003.

"Reducing Needlestick Injuries in the Operating Room" Sales/Product Literature 2001.

Bergdahl et al. "Studies on Coagulation and the Development of an Automatic Computerized Bipolar Coagulator" J. Neurosurg, vol. 75, Jul. 1991, pp. 148-151.

Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.

Sayfan et al. "Sutureless Closed Hemorrhoidectomy: A New Technique" Annals of Surgery vol. 234 No. 1 Jul. 2001; pp. 21-24.

Levy et al., "Update on Hysterectomy—New Technologies and Techniques" OBG Management, Feb. 2003.

Dulemba et al. "Use of a Bipolar Electrothermal Vessel Sealer in Laparoscopically Assisted Vaginal Hysterectomy" Sales/Product Literature; Jan. 2004.

Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.

Sengupta et al., "Use of a Computer-Controlled Bipolar Diathermy System in Radical Prostatectomies and Other Open Urological Surgery" ANZ Journal of Surgery (2001) 71.9 pp. 538-540.

Rothenberg et al. "Use of the LigaSure Vessel Sealing System in Minimally Invasive Surgery in Children" Int'l Pediatric Endosurgery Group (IPEG) 2000.

Crawford et al. "Use of the LigaSure Vessel Sealing System in Urologic Cancer Surgery" Grand Rounds in Urology 1999 vol. 1 Issue 4 pp. 10-17.

Craig Johnson, "Use of the LigaSure Vessel Sealing System in Bloodless Hemorrhoidectomy" Innovations That Work, Mar. 2000.

Levy et al. "Use of a New Energy-based Vessel Ligation Device During Vaginal Hysterectomy" Int'l Federation of Gynecology and Obstetrics (FIGO) World Congress 1999.

Barbara Levy, "Use of a New Vessel Ligation Device During Vaginal Hysterectomy" FIGO 2000, Washington, D.C.

E. David Crawford "Use of a Novel Vessel Sealing Technology in Management of the Dorsal Veinous Complex" Sales/Product Literature 2000.

Jarrett et al., "Use of the LigaSure Vessel Sealing System for Peri-Hilar Vessels in Laparoscopic Nephrectomy" Sales/Product Literature 2000.

Crouch et al. "A Velocity-Dependent Model for Needle Insertion in Soft Tissue" MICCAI 2005; LNCS 3750 pp. 624-632, Dated: 2005.

McLellan et al. "Vessel Sealing for Hemostasis During Pelvic Surgery" Int'l Federation of Gynecology and Obstetrics FIGO World Congress 2000, Washington, D.C.

McLellan et al. "Vessel Sealing for Hemostasis During Gynecologic Surgery" Sales/Product Literature 1999.

(56) References Cited

OTHER PUBLICATIONS

U.S. Appl. No. 08/926,869, filed Sep. 10, 1997, James G. Chandler.
U.S. Appl. No. 09/177,950, filed Oct. 23, 1998, Randel A. Frazier.
U.S. Appl. No. 09/387,883, filed Sep. 1, 1999, Schmaltz et al.
U.S. Appl. No. 09/591,328, filed Jun. 9, 2000, Ryan et al.
U.S. Appl. No. 12/336,970, filed Dec. 17, 2008, Sremcich et al.
U.S. Appl. No. 13/731,674, filed Dec. 31, 2012, Siebrecht.

* cited by examiner

END EFFECTOR ASSEMBLIES AND
METHODS OF MANUFACTURING END
EFFECTOR ASSEMBLIES FOR TREATING
AND/OR CUTTING TISSUE

CROSS REFERENCE TO RELATED
APPLICATION

The present application claims the benefit of and priority to U.S. Provisional Application Ser. No. 61/829,415, filed on May 31, 2013, the entire contents of which are incorporated herein by reference.

BACKGROUND

Technical Field

The present disclosure relates to surgical devices and, more particularly, to end effector assemblies for energy-based surgical devices and methods of manufacturing end effector assemblies for energy-based surgical devices.

Background of Related Art

A surgical forceps is a plier-like device which relies on mechanical action between its jaws to grasp, clamp, and constrict tissue. Energy-based surgical forceps utilize both mechanical clamping action and energy to affect hemostasis by heating tissue to coagulate and/or cauterize tissue. Certain surgical procedures require more than simply cauterizing tissue and rely on the unique combination of clamping pressure, precise energy control and gap distance (i.e., distance between opposing jaw members when closed about tissue) to "seal" tissue. Typically, once tissue is sealed, the surgeon has to accurately sever the tissue along the newly formed tissue seal. Accordingly, many tissue sealing devices have been designed which incorporate a knife or blade member which effectively severs the tissue after forming a tissue seal. More recently, tissue sealing devices have incorporated energy-based cutting features for energy-based tissue division.

SUMMARY

As used herein, the term "distal" refers to the portion that is being described which is further from a user, while the term "proximal" refers to the portion that is being described which is closer to a user. Further, to the extent consistent, any of the aspects described herein may be used in conjunction with any or all of the other aspects described herein.

In accordance with the present disclosure, a method of manufacturing an end effector assembly including first and second energizable portions configured to supply energy to tissue is provided. The method includes forming a substrate including first and second portions interconnected by a connector portion. The substrate is formed as a single integrated component. The method further includes engaging the substrate with an insulative member, and removing the connector portion of the substrate to electrically insulate the first and second portions from one another.

In some aspects of the present disclosure, the substrate is an electrically-conductive plate.

In some aspects of the present disclosure, the substrate is formed via stamping.

In some aspects of the present disclosure, the substrate is engaged to the insulative member via overmolding.

In some aspects of the present disclosure, the substrate includes one or more flanges for overmolding the substrate onto the insulative member.

In some aspects of the present disclosure, the insulative member forms an outer insulative housing supporting the substrate and an insulative spacer disposed between the first and second portions.

In some aspects of the present disclosure, the method further includes perforating the substrate where each of the first and second portions meet the connector portion to facilitate removal of the connector portion.

In some aspects of the present disclosure, the method further includes engaging the insulative member, having the substrate engaged thereon, about a frame.

In some aspects of the present disclosure, the method further includes independently connecting the first and second portions to a source of energy.

In accordance with the present disclosure, a method of manufacturing a jaw member of a surgical forceps is provided. The method includes forming a conductive plate including a first portion configured for supplying energy to tissue to treat tissue, a second portion configured for supplying energy to tissue to cut tissue, and a connector portion interconnecting the first and second portions. The plate is formed as a single integrated component. The method further includes engaging the plate with an insulative housing to form a first jaw member, and removing the connector portion of the plate to electrically insulate the first and second portions from one another.

In some aspects of the present disclosure, the plate is formed via stamping.

In some aspects of the present disclosure, the plate is engaged to the insulative housing via overmolding. Further, the plate may include one or more flanges for overmolding the plate onto the insulative housing.

In some aspects of the present disclosure, the insulative housing serves as an insulative spacer disposed between the first and second portions.

In some aspects of the present disclosure, the method further includes perforating the plate where each of the first and second portions meet the connector portion to facilitate removal of the connector portion.

In some aspects of the present disclosure, the method further includes engaging the first jaw member about a first jaw frame. The method may additionally include pivotably coupling the first jaw frame to a second jaw frame such that the first and second jaw frames are movable relative to one another to grasp tissue between the first jaw member and a second jaw member disposed about the second jaw frame.

In some aspects of the present disclosure, the method further includes independently connecting the first and second portions to a source of energy.

BRIEF DESCRIPTION OF THE DRAWINGS

Various aspects and features of the present disclosure are described herein with reference to the drawings wherein.

DETAILED DESCRIPTION

Figure 1:
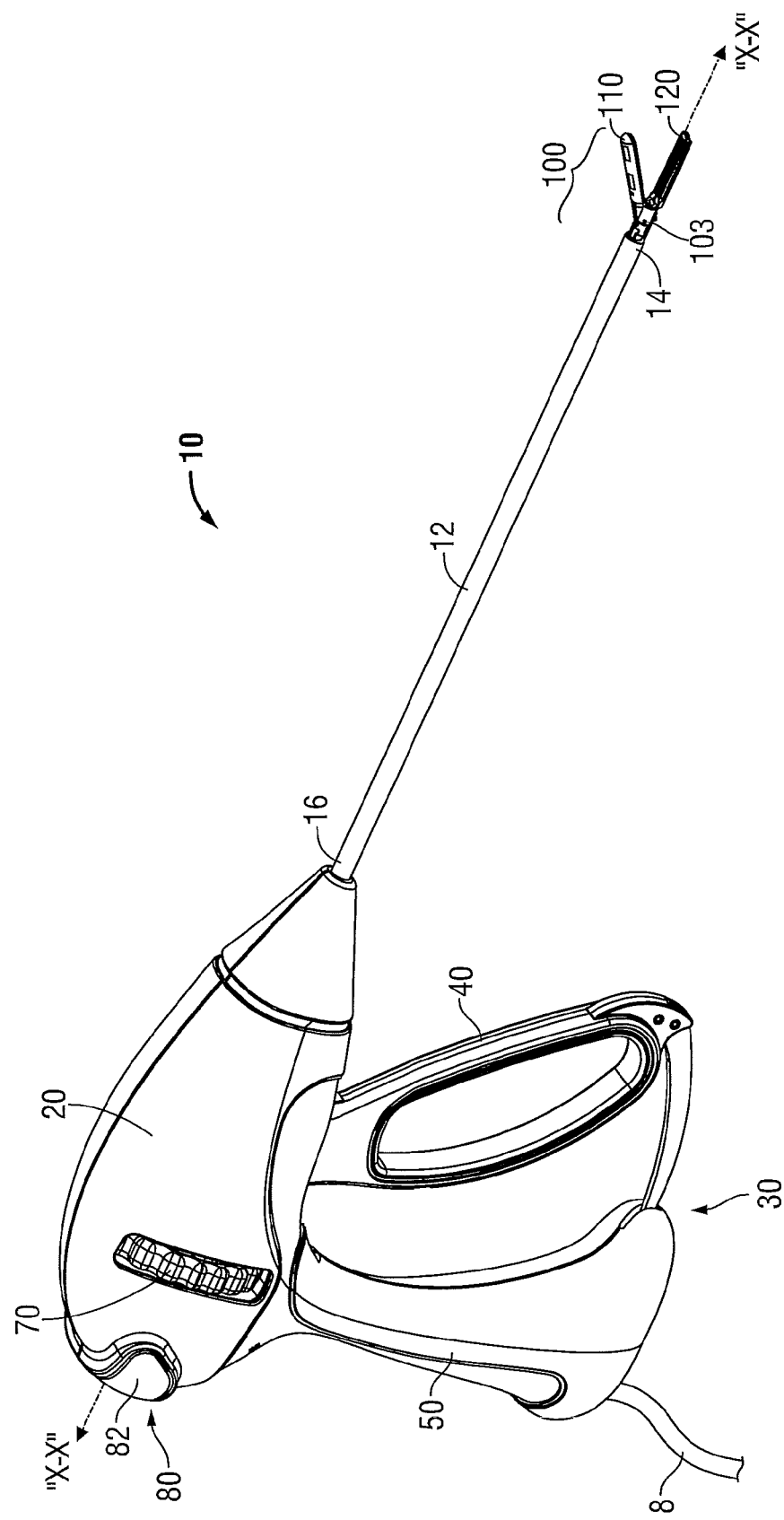
FIG. 1 is a front, side, perspective view of an endoscopic surgical forceps configured for use in accordance with the present disclosure.
Figure 2:
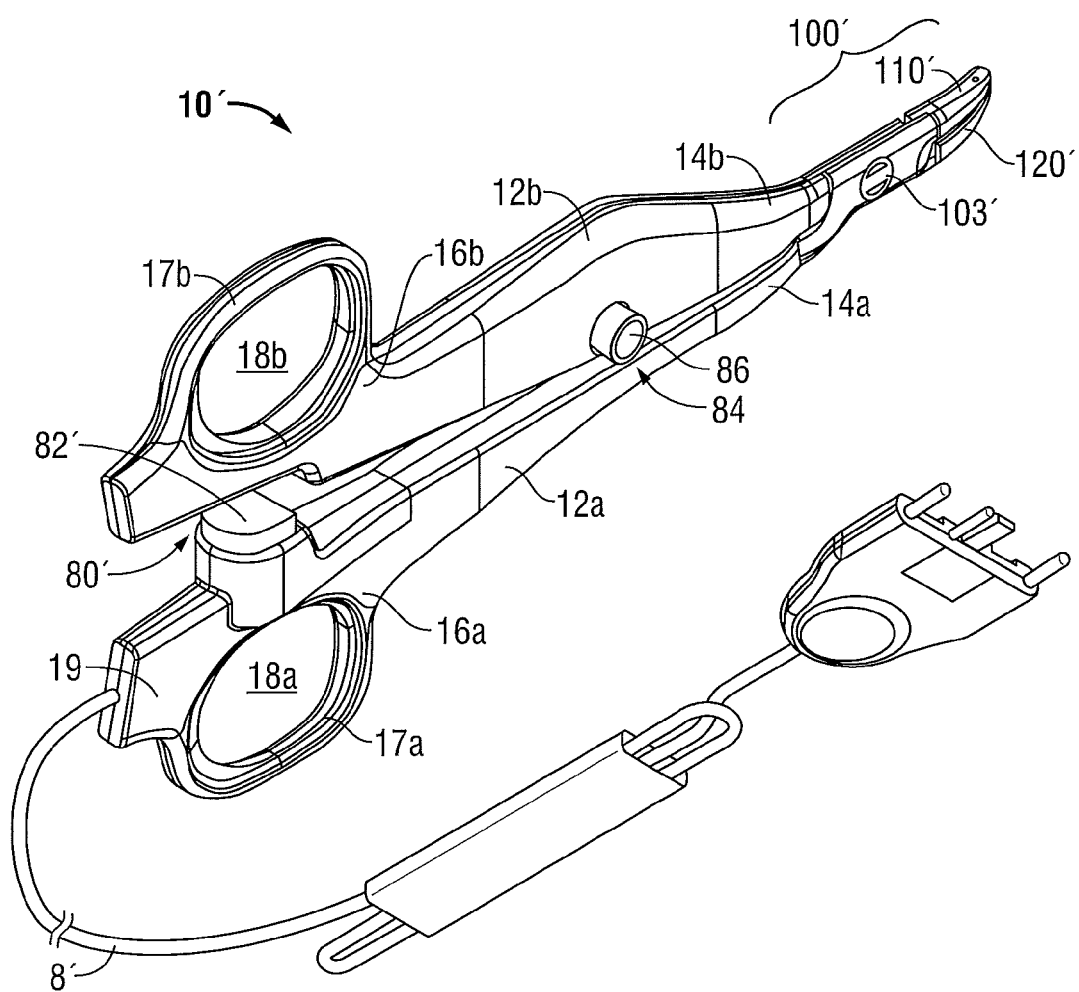
FIG. 2 is a front, side, perspective view of an open surgical forceps configured for use in accordance with the present disclosure.

Turning to FIGS. 1 and 2, FIG. 1 depicts a forceps 10 for use in connection with endoscopic surgical procedures and FIG. 2 depicts an open forceps 10' contemplated for use in connection with traditional open surgical procedures. For the purposes herein, either an endoscopic device, e.g., forceps 10, an open device, e.g., forceps 10', or any other suitable surgical device may be utilized in accordance with the present disclosure. Obviously, different electrical and mechanical connections and considerations apply to each particular type of device, however, the aspects and features of the present disclosure remain generally consistent regardless of the particular device used.

Referring to FIG. 1, an endoscopic forceps 10 is provided defining a longitudinal axis "X-X" and including a housing 20, a handle assembly 30, a rotating assembly 70, an activation assembly 80, and an end effector assembly 100. Forceps 10 further includes a shaft 12 having a distal end 14 configured to mechanically engage end effector assembly 100 and a proximal end 16 that mechanically engages housing 20. Forceps 10 also includes cable 8 that connects forceps 10 to an energy source (not shown), e.g., a generator or other suitable power source, although forceps 10 may alternatively be configured as a battery-powered device. Cable 8 includes a wire (or wires) (not shown) extending therethrough that has sufficient length to extend through shaft 12 in order to provide energy to at least one of tissue-contacting plates 114, 124 (FIG. 3A) of jaw members 110, 120, respectively, as well as to energy-based cutting member 130 (FIG. 3A) of jaw member 120. Activation assembly 80 includes a two-mode activation switch 82 provided on housing 20 for selectively supplying energy to jaw members 110, 120 for treating, e.g., sealing, tissue (the first mode), and for energy-based tissue cutting (the second mode).

Handle assembly 30 includes fixed handle 50 and a movable handle 40. Fixed handle 50 is integrally associated with housing 20 and handle 40 is movable relative to fixed handle 50. Movable handle 40 of handle assembly 30 is operably coupled to a drive assembly (not shown) that, together, mechanically cooperate to impart movement of jaw members 110, 120 between a spaced-apart position and an approximated position to grasp tissue between jaw members 110, 120. More specifically, as shown in FIG. 1, movable handle 40 is initially spaced-apart from fixed handle 50 and, correspondingly, jaw members 110, 120 are disposed in the spaced-apart position. Movable handle 40 is depressible from this initial position to a depressed position corresponding to the approximated position of jaw members 110, 120. Rotating assembly 70 is rotatable in either direction about longitudinal axis "X-X" to rotate end effector 100 about longitudinal axis "X-X."

Referring to FIG. 2, an open forceps 10' is shown including two elongated shaft members 12a, 12b, each having a proximal end 16a, 16b, and a distal end 14a, 14b, respectively. Forceps 10' is configured for use with an end effector assembly 100' similar to end effector assembly 100 (FIG. 1). More specifically, end effector assembly 100' includes first and second jaw members 110', 120' attached to respective distal ends 14a, 14b of shaft members 12a, 12b. Jaw members 110', 120' are pivotably connected about a pivot 103'. Each shaft member 12a, 12b includes a handle 17a, 17b disposed at the proximal end 16a, 16b thereof. Each handle 17a, 17b defines a finger hole 18a, 18b therethrough for receiving a finger of the user. As can be appreciated, finger holes 18a, 18b facilitate movement of the shaft members 12a, 12b relative to one another to, in turn, pivot jaw members 110', 120' from an open position, wherein jaw members 110', 120' are disposed in spaced-apart relation relative to one another, to a closed position, wherein jaw members 110', 120' cooperate to grasp tissue therebetween.

One of the shaft members 12a, 12b of forceps 10', e.g., shaft member 12a, includes a proximal shaft connector 19 configured to connect the forceps 10' to a source of energy (not shown), e.g., a generator. Proximal shaft connector 19 secures a cable 8' to forceps 10' such that the user may selectively supply energy to jaw members 110', 120' for treating, e.g., sealing, tissue, and for energy-based tissue cutting. More specifically, a first activation assembly 80' is provided for supplying energy to jaw members 110', 120' to treat tissue upon sufficient approximation of shaft members 12a, 12b, e.g., upon activation of activation button 82' via shaft member 12b. A second activation assembly 84 including a selectively depressible activation button 86 is provided on one of the shaft members 12a, 12b, e.g., shaft member 12b, for selectively supplying energy jaw members 110', 120' for energy-based tissue cutting.

Figure 3A:
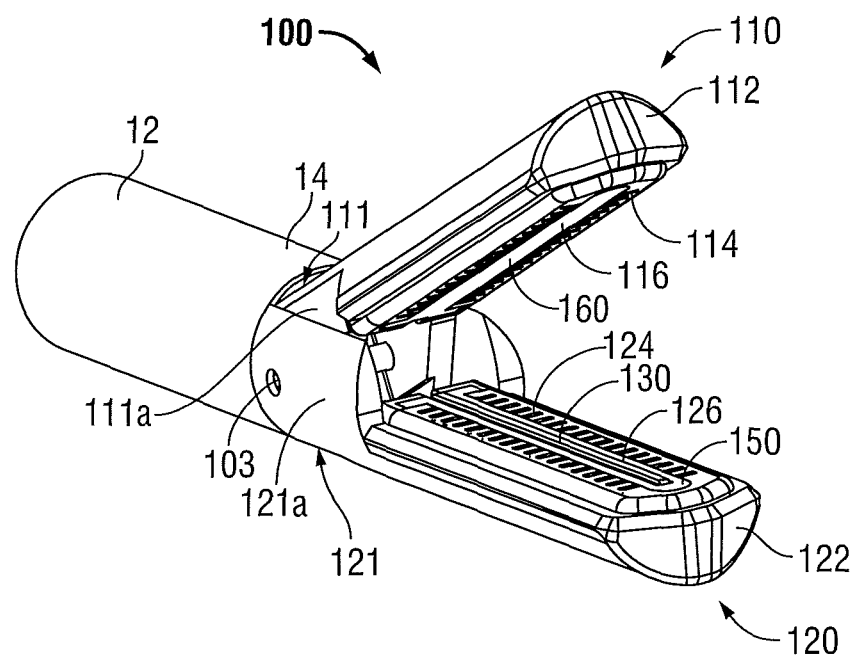
FIG. 3A is a front, side, perspective view of an end effector assembly configured for use with the forceps of FIG. 1 or 2.
Figure 3B:
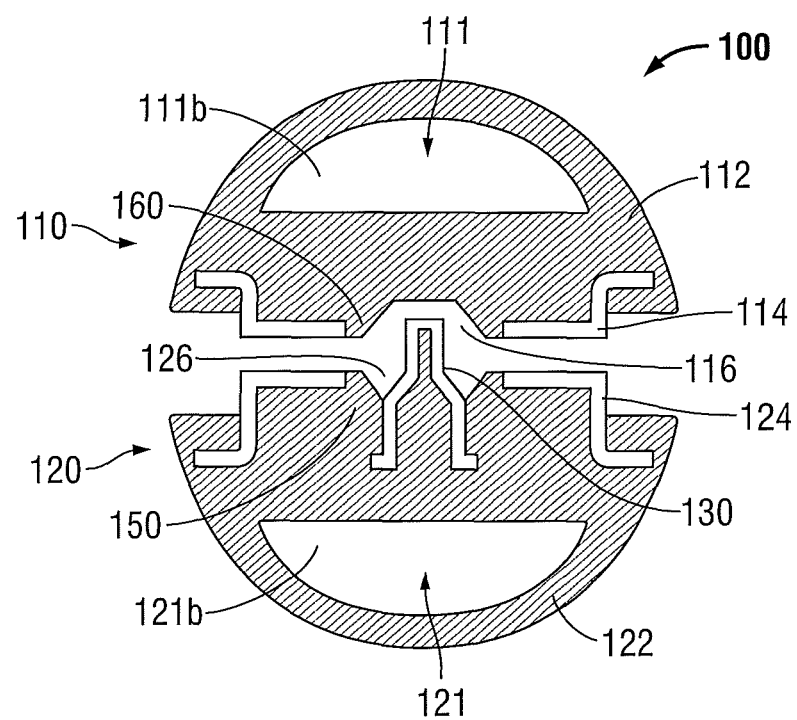
FIG. 3B is a transverse, cross-sectional view of the end effector assembly of FIG. 3A.

With reference to FIGS. 3A and 3B, end effector assembly 100 of forceps 10 (FIG. 1) is shown, although end effector assembly 100 may similarly be used in conjunction with forceps 10' (FIG. 2), or any other suitable surgical device. For purposes of simplicity, end effector assembly 100 is described herein as configured for use with forceps 10 (FIG. 1).

Each jaw member 110, 120 of end effector assembly 100 includes a jaw frame 111, 121, an outer insulative jaw housing 112, 122, and a tissue-contacting plate 114, 124, respectively. Further, one of the jaw members 110, 120, e.g., jaw members 120, includes an energy-based cutting member 130 disposed thereon. Jaw frames 111, 121 each include a proximal flange portion 111a, 121a (FIG. 3A) and a distal extension portion 111b, 121b (FIG. 3B), respectively. Proximal flange portions 111a, 121a of jaw frames 111, 121, respectively, are pivotably coupled to one another about pivot 103 for moving jaw members 110, 120 between the spaced-apart and approximated positions. Distal extension portions 111b, 121b of jaw frames 111, 121 are configured to support jaw housings 112, 122, and tissue-contacting plates 114, 124, respectively, thereon.

Outer insulative jaw housings 112, 122 of jaw members 110, 120 are disposed about distal extension portions 111b, 121b of jaw frames 111, 121 and support and retain tissue-contacting plates 114, 124 on respective jaw members 110, 120 in opposed relation relative to one another. Outer insulative jaw housing 122 of jaw member 120 further supports and retains energy-based cutting member 130 on jaw member 120. Tissue-contacting plates 114, 124 are formed from an electrically conductive material, e.g., for conducting electrical energy therebetween for treating tissue, although tissue-contacting plates 114, 124 may alternatively be configured to conduct any suitable energy through tissue grasped therebetween for energy-based tissue treatment, e.g., tissue sealing. Energy-based cutting member 130 is likewise formed from an electrically conductive material, e.g., for conducting electrical energy between energy-based cutting member 130 and one or both of tissue-contacting plates 114, 124 for electrically cutting tissue, although energy-based cutting member 130 may alternatively be configured to conduct any suitable energy through tissue for electrically cutting tissue.

Tissue-contacting plates 114, 124 are coupled to activation switch 82 (FIG. 1) and the source of energy (not shown), e.g., via the wires (not shown) extending from cable 8 (FIG. 1) through forceps 10 (FIG. 1), such that energy may be selectively supplied to tissue-contacting plate 114 and/or tissue-contacting plate 124 and conducted therebetween and through tissue disposed between jaw members 110, 120 to treat, e.g., seal, tissue in a first mode of operation. Likewise, cutting member 130 is coupled to activation switch 82 (FIG. 1) and the source of energy (not shown), e.g., via the wires (not shown) extending from cable 8 (FIG. 1) through forceps 10 (FIG. 1), such that energy may be selectively supplied to cutting member 130 and conducted through tissue disposed between jaw members 110, 120 to either or both of tissue-contacting plates 114, 124 to cut tissue in a second mode of operation.

Continuing with reference to FIGS. 3A and 3B, cutting member 130 is retained within and extends from a first insulating member 150 disposed within a longitudinal slot 126 defined within tissue-contacting plate 124 of jaw member 120. More specifically, first insulating member 150 surrounds cutting member 130 to insulate tissue-contacting plate 124 and cutting member 130 from one another. A second insulating member 160 is disposed within a longitudinal slot 116 defined within tissue-contacting plate 114 of jaw member 110 to oppose cutting member 130. Second insulating member 160 insulates cutting member 130 from tissue-contacting plate 114 of jaw member 110 when jaw members 110, 120 are disposed in the approximated position. As will be described in greater detail below, first and second insulating members 160, 150 may be integrally formed as portions of respective outer insulative jaw housings 112, 122 or may be formed as separate components engaged to outer insulative jaw housings 112, 122, respectively.

As described above, end effector assembly 100 includes first and second jaw members 110, 120, each including a tissue-contacting plate 114, 124 having a longitudinal slot 116, 126, respectively, extending therethrough. Cutting member 130 is disposed within longitudinal slot 126 of jaw member 120 and opposes longitudinal slot 116 of jaw member 110. Ensuring proper alignment and spacing between cutting member 130 and tissue-contacting plate 124 helps reduce current concentrations and provides a more uniform distribution of current flow from cutting member 130, through tissue, to tissue-contacting plate 124 and/or tissue-contacting plate 114. As a result, effective energy-based tissue cutting can be more readily achieved and damage to surrounding tissue can be minimized. Further, proper alignment and spacing between cutting member 130 and tissue-contacting plate 124 not only facilitates electrical cutting, but also facilitates the formation of an effective tissue seal and minimizes damage to surrounding tissue during conduction of energy between tissue-contacting plates 114, 124.

Turning now to FIGS. 4A-4C and 5A-5C, methods of manufacturing one or more components of an end effector assembly of an energy-based surgical device are described. As can be appreciated in view of the following, these manufacturing methods help ensure proper alignment and spacing between the various components of the end effector assembly, thereby facilitating effective tissue treatment and/or cutting. For the purposes herein, manufacture of a jaw member similar to jaw member 120 is described below with reference to FIGS. 4A-4C and 5A-5C. However, the manufacturing methods provided in accordance with the present disclosure are equally applicable for use in manufacturing an end effector assembly or component thereof of any suitable energy-based surgical device.

Figure 4A:
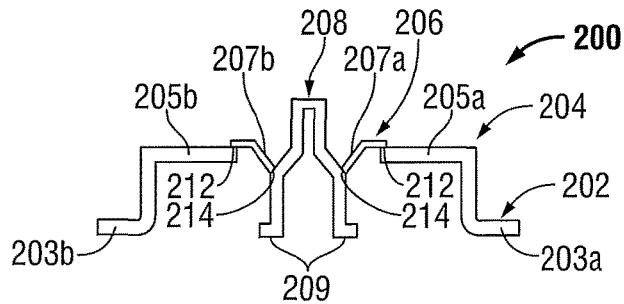
FIGS. 4A-4C are transverse-cross-sectional views illustrating the manufacture of a jaw member of an end effector assembly similar to the end effector assembly of FIG. 3A, in accordance with the present disclosure.
Figure 5A:
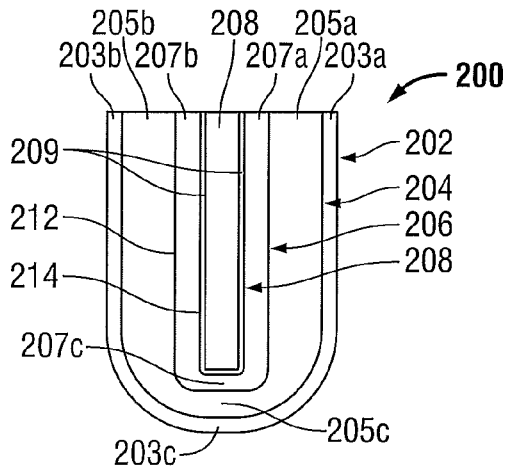
FIGS. 5A-5C are top views illustrating the manufacture of the jaw member of FIGS. 4A-4C.

Initially, as shown in FIGS. 4A and 5A, an electrically-conductive substrate 200 (or other suitable substrate configured to energize tissue for treating and/or cutting tissue) is formed. Substrate 200 may be formed via, for example, stamping, although substrate 200 may alternatively be formed via molding, punching, blanking, embossing, coining, or other suitable method. Substrate 200 is formed as a single, integral component and includes: a generally U-shaped outer engagement flange 202 defining first and second side portions 203*a*, 203*b* interconnected by an arc-shaped portion 203*c*; a generally U-shaped tissue-contacting segment 204 extending inwardly from outer engagement flange 202 and defining first and second side portions 205*a*, 205*b* interconnected by an arc-shaped portion 205*c*; a generally U-shaped connector 206 extending inwardly from tissue-contacting segment 204 and defining first and second side portions 207*a*, 207*b* interconnected by an arc-shaped portion 207*c*; and a central member 208 disposed between side portions 207*a*, 207*b* and arc-shaped portion 207*c* of tissue-contact segment 204. Central member 208 defines an inner engagement flange 209 extending therefrom.

As shown in FIGS. 4A and 5A, once substrate 200 is formed (or during formation of substrate 200), perforations 212, 214 may be formed in substrate 200 between tissue-contacting segment 204 and connector 206, and between connector 206 and central member 208, respectively.

Figure 4B:
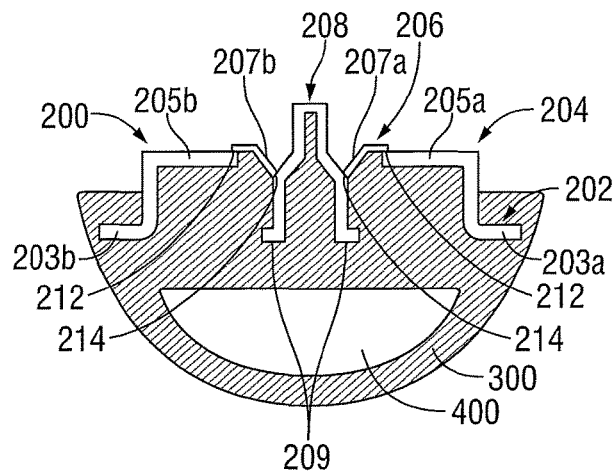
Figure 5B:
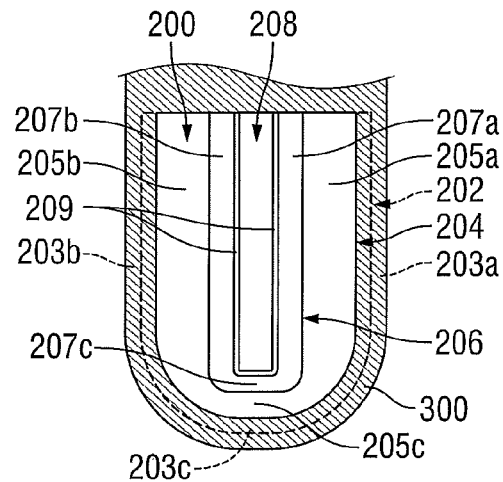

Referring to FIGS. 4B and 5B, substrate 200, once formed (and/or perforated), is engaged to, e.g., retained and supported on, insulative member 300. More specifically substrate 200 may be engaged to insulative member 300 via overmolding insulative member 300 about substrate 200 such that outer flange 202 and inner flange 209 are retained within and surrounded by insulative member 300. Alternatively, substrate 200 may be engaged to insulative member 300 via snap-fitting, adhesion, or any other suitable method. Prior to, in conjunction with, or after engagement of substrate 200 and insulative member 300 to one another, insulative member 300 is engaged about jaw frame 400. For example, insulative member 300 may be injection molded about both jaw frame 400 and substrate 200 to simultaneously (or near-simultaneously) engage the components to one another. Alternatively, insulative member 300 may be engaged about jaw frame 400, e.g., via snap-fitting, friction fitting, etc., after engagement of insulative member 300 about substrate 200.

Figure 4C:
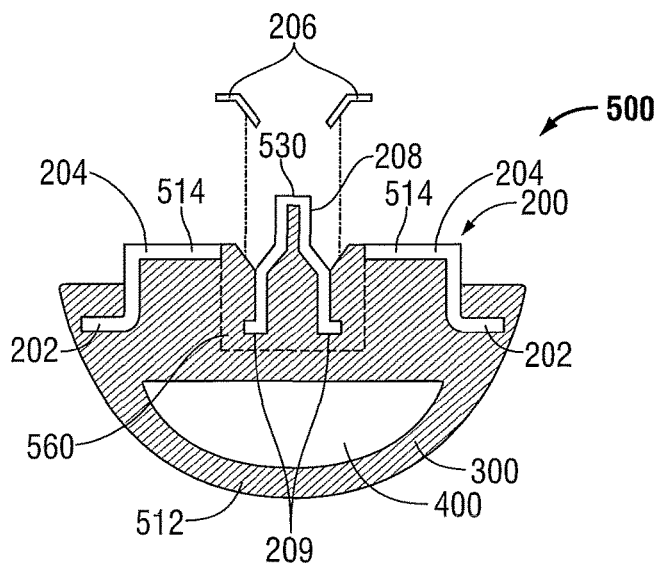
Figure 5C:
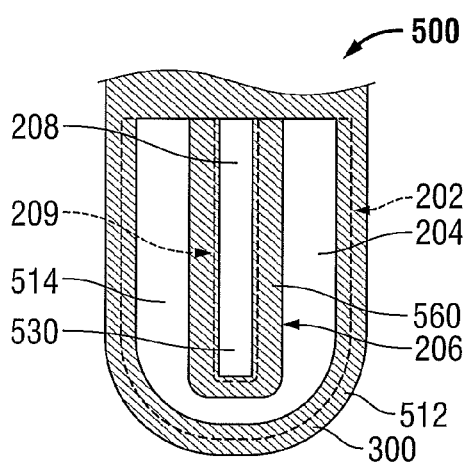

Turning now to FIGS. 4C and 5C, with insulative member 300 engaged about both substrate 200, e.g., via the engagement of outer and inner flanges 202, 209 within member 300, and jaw frame 400, substrate 200 is retained in fixed position and orientation relative to itself and to insulative member 300. In other words, the alignment and spacing of the various portions of substrate 200 is set. At this point, substrate 200 may be partitioned by removing connector 206 without disturbing the set alignment and spacing between the various portions of substrate 200. Removal of connector 206 is facilitated by perforations 212, 214 (FIGS. 4A, 4B, 5A, and 5B). With connector 206 removed, as shown in FIGS. 4C and 5C, central member 208 is decoupled from tissue-contacting segment 204. More specifically, upon removal of connector 206, central member 208 and tissue-contacting segment 204 are spaced-apart and insulated from one another via insulative member 300.

As shown in FIGS. 4C and 5C, and by the above-described manufacturing method, a jaw member 500 including a tissue-contacting plate 514 and energy-based cutting member 530 electrically insulated from one another via an insulating member 560 is provided. Advantageously, tissue-contacting plate 514 and energy-based cutting member 530 are properly aligned and spaced relative to one another, thus facilitating effective tissue treatment and/or cutting during use. Further, as can be appreciated in view of the above, insulating member 560 and outer insulative jaw housing 512 are formed as a single, integral component. However, it is also envisioned that insulating member 560 and outer insulative jaw housing 512 be provided as separate components.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method of manufacturing an end effector assembly including first and second energizable portions configured to supply energy to tissue, the method comprising:
   forming a substrate including first and second portions interconnected by a connector portion, the substrate formed as a single integrated component, the connector portion including first and second side portions interconnected by an arc-shaped portion;
   engaging the substrate with an insulative member; and
   removing the connector portion of the substrate to electrically insulate the first and second portions from one another.

2. The method according to claim 1, wherein the substrate is an electrically-conductive plate.

3. The method according to claim 1, wherein the substrate is formed via stamping.

4. The method according to claim 1, wherein the substrate is engaged to the insulative member via overmolding.

5. The method according to claim 4, wherein the substrate includes at least one flange for overmolding the substrate onto the insulative member.

6. The method according to claim 1, wherein the insulative member forms an outer insulative housing supporting the substrate and an insulative spacer disposed between the first and second portions.

7. The method according to claim 1, further comprising the step of perforating the substrate where each of the first and second portions meet the connector portion to facilitate removal of the connector portion.

8. The method according to claim 1, further comprising the step of engaging the insulative member, having the substrate engaged thereon, about a frame.

9. The method according to claim 1, further comprising the step of independently connecting the first and second portions to a source of energy.

10. A method of manufacturing a jaw member of a surgical forceps, comprising:
    forming a conductive plate including a first portion configured for supplying energy to tissue to treat tissue, a second portion configured for supplying energy to tissue to cut tissue, and a connector portion interconnecting the first and second portions and including first and second side portions, the second portion disposed between the first and second side portions of the connector, the plate formed as a single integrated component;
    engaging the plate with an insulative housing to form a first jaw member; and
    removing the connector portion of the plate to electrically insulate the first and second portions from one another.

11. The method according to claim 10, wherein the plate is formed via stamping.

12. The method according to claim 10, wherein the plate is engaged to the insulative housing via overmolding.

13. The method according to claim 10, wherein the plate includes at least one flange for overmolding the plate onto the insulative housing.

14. The method according to claim 10, wherein the insulative housing serves as an insulative spacer disposed between the first and second portions.

15. The method according to claim 10, further comprising the step of perforating the plate where each of the first and second portions meet the connector portion to facilitate removal of the connector portion.

16. The method according to claim 10, further comprising the step of engaging the first jaw member about a first jaw frame.

17. The method according to claim 16, further comprising the step of pivotably coupling the first jaw frame to a second jaw frame such that the first and second jaw frames are movable relative to one another to grasp tissue between the first jaw member and a second jaw member disposed about the second jaw frame.

18. The method according to claim 10, further comprising the step of independently connecting the first and second portions to a source of energy.

19. The method according to claim 1, wherein each of the first and second side portions of the connector have a first end portion and a second end portion, the arc-shaped portion directly connected to the second end portions of each of the first and second side portions.

20. The method according to claim 19, wherein the first and second side portions are oriented parallel to one another.

* * * * *